(12) United States Patent
Kuo

(10) Patent No.: US 10,590,184 B2
(45) Date of Patent: Mar. 17, 2020

(54) PROCESS FOR A PREPARATION OF THE MODIFIED PORCINE PLASMA FIBRONECTIN FOR ENHANCE WOUND HEALING

(71) Applicant: National Yang Ming University, Taipei (TW)

(72) Inventor: Jean-Cheng Kuo, Taipei (TW)

(73) Assignee: NATIONAL YANG-MING UNIVERSITY, Taipei (TW)

( * ) Notice: Subject to any disclaimer, the term of this patent is extended or adjusted under 35 U.S.C. 154(b) by 103 days.

(21) Appl. No.: 15/713,113

(22) Filed: Sep. 22, 2017

(65) Prior Publication Data

US 2018/0127484 A1 May 10, 2018

Related U.S. Application Data

(60) Provisional application No. 62/399,688, filed on Sep. 26, 2016.

(51) Int. Cl.
| | |
|---|---|
| C07K 14/78 | (2006.01) |
| A61L 26/00 | (2006.01) |
| A61K 9/00 | (2006.01) |
| A61K 38/39 | (2006.01) |
| C12Q 1/37 | (2006.01) |

(52) U.S. Cl.
CPC ............ *C07K 14/78* (2013.01); *A61K 9/0014* (2013.01); *A61K 38/39* (2013.01); *A61L 26/0047* (2013.01); *A61L 26/0066* (2013.01); *C12Q 1/37* (2013.01); *A61L 2300/21* (2013.01); *A61L 2300/252* (2013.01); *A61L 2300/254* (2013.01); *A61L 2300/412* (2013.01)

(58) Field of Classification Search
None
See application file for complete search history.

(56) References Cited

U.S. PATENT DOCUMENTS

2007/0160543 A1* 7/2007 Moller .................... A61J 1/067
424/46

* cited by examiner

*Primary Examiner* — Erin M. Bowers
(74) *Attorney, Agent, or Firm* — Muncy, Geissler, Olds & Lowe, PC

(57) ABSTRACT

This invention reveals the potential applications of modified porcine plasma fibronectin that could be applied as a safe material for clinical wound healing and tissue repair. In order to seek safe sources of plasma fibronectin for practical consideration in wound dressing, this invention isolated and modified fibronectin from porcine plasma and demonstrated that modified porcine plasma fibronectin has similar ability as homo plasma fibronectin being as a suitable substrate for stimulation of cell adhesion and directed cell migration. The present invention also reveals a material and a pharmaceutical composition enhance wound healing.

8 Claims, 14 Drawing Sheets

Specification includes a Sequence Listing.

Porcine plasma (20 ml)

⇩

Gelatin-Sepharose Fast Flow 4B

1. Loading
2. TBS-EDTA 50 ml wash
3. 1 M NaCl 50 ml wash
4. < 0.5 M Arg 50 ml wash
5. > 0.5 M Arg elute

⇩

Dialyze in TBS (pH 5-8 ) 24h, 4 C

Porcine plasma fibronectin (7.14 mg)

Porcine plasma (20 ml)

Gelatin-Sepharose Fast Flow 4B

1. Loading
2. TBS-EDTA 50 ml wash
3. 1 M NaCl 50 ml wash
4. < 0.5 M Arg 50 ml wash
5. > 0.5 M Arg elute Dialyze in TBS (pH 5-8 ) 24h, 4 C ⇒ Gelatin
⇌ Arg
· Small particle
● Unbounded particle
● Non-specific binding
⋐ Fibronectin Porcine plasma fibronectin (7.14 mg)

PROCESS FOR A PREPARATION OF THE MODIFIED PORCINE PLASMA FIBRONECTIN FOR ENHANCE WOUND HEALING

CROSS-REFERENCE TO RELATED APPLICATIONS

The present application claims the benefit of priority of U.S. Provisional Patent Application No. 62/399,688, entitled "Fibronectin in cell adhesion and migration via N-glycosylation," filed Sep. 26, 2016, which is incorporated herein by reference for all purposes.

FIELD OF THE INVENTION

The present invention relates to a preparation of modified porcine plasma fibronectin that could be applied as a safe material for clinical wound healing and tissue repair. The present invention also reveals a material and a pharmaceutical composition enhance wound healing.

BACKGROUND OF THE INVENTION

Wound healing is a dynamic process, which consists of hemostasis, inflammation, proliferation and remodeling. Fibronectin, an extracellular matrix (ECM) glycoprotein, plays important roles in different stages of wound healing, with the main function being cellular adhesion and mediation of cell migration. Fibronectin interacts and activates cell surface integrin receptors, which in turn recruits a series of cellular proteins to connect with the actin cytoskeleton inside the cell, initiating the formation of integrin based adhesive organelles, focal adhesions (FAs). The coupling of actin cytoskeleton and ECM fibronectin via FAs dynamically drives directed cell migration in wound healing. At the beginning, cell protrusions characterized by actin polymerization into dense actin network are extended in the direction of migration followed by attachment of the protrusions to ECM fibronectin that forms nascent adhesions (new-born FAs). Subsequently, nascent adhesions become matured and growing in size via myosin II-mediated contractile forces transduced along the bundled actin filaments. Mature FAs transduce contractile forces from the actin cytoskeleton to the ECM fibronectin, thereby pulling the cell body forward. Finally, FA disassembly accompanied with myosin II-driven contractile forces retracts the trailing edge of the cell from the ECM fibronectin. The ECM fibronectin outside the cell links to the actin cytoskeleton inside the cell via FAs in association with the dynamic control of cell adhesion and directed cell migration in wound healing.

There are two forms of fibronectin: plasma fibronectin and cellular fibronectin. Plasma fibronectin is synthesized by hepatocytes into the blood plasma, while cellular fibronectin is produced by many cell types such as fibroblasts, endothelial cells, myocytes and chondrocytes. In wound healing, it has been reported that plasma fibronectin accumulates remarkably in the wound after wounding in vivo, which is crucial for various functions of platelets, fibroblasts and endothelial cells such as adhesion, migration and aggregation, revealing that plasma fibronectin is likely to serve as a suitable substrate to accelerate wound repair in vivo. Indeed, in animal model, provisional matrix containing plasma fibronectin significantly supports epidermal cell adhesion and migration in the re-epithelialization process, showing the clinical potential of plasma fibronectin in human wound healing and tissue repair.

However, the application of plasma fibronectin to human wound healing has not been validated due to the unreliable and expensive sources of human plasma. The fibronectin from human is not suitable for use in medical products because the fibronectin in a cancer patient has a specific abnormal glycosylation modification, which has the effect of promoting cancer metastasis. Therefore, it will lead to medical risks that use the high purity fibronectin from the blood of unknown health donors to other people. In previous publications, the method includes the recombinant of fibronectin proteins by gene recombination and the purification of fibronectin from human blood is flawed. The inventor has demonstrated that the glycans on fibronectin plays an important role in promoting the progress of wound healing, whereas fibronectin, which is expressed by gene recombination, does not contain glycosylation modification, so its effect is a gap.

SUMMARY OF THE INVENTION

Given the importance of plasma fibronectin to wound healing and its potentials in medical application, the inventor set to isolate and modify fibronectin from porcine (porcine plasma fibronectin). The inventor has confirmed that porcine plasma fibronectin can be substitute for human plasma fibronectin to wound healing with better safety and quantity.

As mentioned earlier, the purified fibronectin from human blood has safety concerns, and in our study also found that human fibronectin and porcine fibronectin with similar N-glycan structures on different N-glycosylation sites, and the function are similar.

With further improvement, the development of porcine fibronectin in medical applications can be substitute for human fibronectin with better function and solve the problem from human fibronectin. The inventor has characterized the N-glycosylation sites and N-glycan structures on homo and porcine plasma fibronectin. The inventor found that N-glycans on plasma fibronectin have a role in positive regulation of cell adhesion and directed cell migration by synergistically promoting integrin-mediated adhesive signals. Therefore, to maintain the glycans on plasma fibronectin during the purification procedure is important. However, in previous published method of the fibronectin purification is too rough and without description of glycans preservation either. So, the invention of process for a preparation of fibronectin isolated from porcine plasma can preserve glycans attached on fibronectin.

The inventor has characterized that the structure of sialic acids on porcine fibronectin are Neu5AC and Neu5GC, while that on human fibronectin is only Neu5AC, revealing the possibility of Neu5GC in causing immune response in human body in clinical application. The inventor has confirmed the limited effect of sialic acids of fibronectin in cell adhesion and directed cell migration, so the invention of process for a preparation of a human-used fibronectin isolated from porcine plasma is to release sialic acids from porcine plasma fibronectin.

In addition, the inventor has confirmed that digested plasma fibronectin has a role in positive regulation of cell adhesion and directed cell migration. Therefore, the invention of process for a preparation of a human-used plasma fibronectin with improved wound-healing ability is to digest fibronectin properly into fibronectin peptides after purification procedure.

To solve the problems, this invention provides a method for enhance wound healing in a subject, wherein the method comprising: administering a modified glycosylation fibronectin from porcine by an enzyme to the subject.

In one embodiment of the invention, the modified glycans are a plurality of sialic acid molecules.

In one embodiment of the invention, the plurality of sialic acid molecules are the N-acetylneuraminic acid (Neu5Ac) and/or the N-glycolylneuraminic acid (Neu5GC) residues.

In one embodiment of the invention, the plurality of sialic acid molecules are removed >80%.

In one embodiment of the invention, the enzyme is the α2-3,6,8 Neuraminidase.

In one embodiment of the invention, the enzyme further comprises a proteinase with ability to digest fibronectin.

In one embodiment of the invention, the proteinase is the matrix metalloproteinase 3.

In one embodiment of the invention, the modified glycosylation porcine fibronectin is prepared by an only one gelatin-Sepharose Fast Flow 4B with proper buffer in glycan preservation.

To solve the problems, this invent provides a pharmaceutical composition for enhance wound healing in a subject, wherein the pharmaceutical composition comprising a modified glycans porcine fibronectin by an enzyme, a collagen, a hyaluronic acid a pharmaceutically acceptable salt thereof.

To solve the problems, this invent provides a material for enhance wound healing in a subject, wherein the material comprising a modified glycans porcine fibronectin by an enzyme, wherein the modified glycans are a plurality of sialic acid molecules, wherein the sialic acid molecules are removed >80%, wherein the enzyme is the α2-3,6,8 Neuraminidase.

This invent provides a method for purify the modified glycosylation porcine fibronectin, comprising: step 1, providing a cleared plasma; step 2, passing the cleared plasma through a pre-column of gelatin-Sepharose Fast Flow 4B; step 3, removing nonspecifically adsorbed proteins to the gel with sequential washing with TBS-EDTA; step 4, removing nonspecifically adsorbed proteins to the gel with sequential washing with 1 M NaCl; step 5, removing nonspecifically adsorbed proteins to the gel with sequential washing with <0.5 M Arginine (Arg); step 6, eluting fibronectin sample with >0.5M Arg.

This invent provides a method for modify the glycosylated porcine fibronectin, comprising: step 1, preparing porcine plasma fibronectin (1 mg) in buffer (pH 5~7); step 2, adding 5~50 units α2-3,6,8 Neuraminidase (One unit is defined as the amount of enzyme required to cleave>95% of the terminal α-Neu5Ac from 1 nmol Neu5Acα2-3Galβ1-3GlcNAcβ1-3Galβ1-4Glc-7-amino-4-methyl-coumarin (AMC), in 5 minutes at 37° C. in a total reaction volume of 10 µl); step 3, incubate for 1~24 hours in 37° C.

This invent provide a method for digest glycosylated porcine fibronectin, comprising: incubating modified porcine plasma fibronectin with matrix metalloproteinase-3 (MMP3) overnight at 37° C. at an enzyme-substrate ratio from 1:5 to 1:30.

This invention isolated and modified fibronectin from porcine plasma and demonstrated that modified porcine plasma fibronectin has similar ability as homo plasma fibronectin being as a suitable substrate for stimulation of cell adhesion and directed cell migration.

This invention reveals the applications of modified porcine plasma fibronectin that could be applied as a safe material for clinical wound healing and tissue repair.

DETAILED DESCRIPTION OF THE INVENTION

In order to seek safe sources of plasma fibronectin for practical consideration in wound dressing, we isolated fibronectin from human (homo) and porcine plasma and demonstrated that porcine plasma fibronectin has similar ability as homo plasma fibronectin being as a suitable substrate for stimulation of cell adhesion and directed cell migration.

This invention further defined N-glycosylation sites and N-glycans on homo and porcine plasma fibronectin. These N-glycosylation modifications on plasma fibronectin that synergistically support integrin-mediated signals are necessary and sufficient in mediating cellular adhesion and directed cell migration. Our study not only determines the important function of N-glycans on both homo and porcine plasma fibronectin mediated cell adhesion and directed cell migration, but also reveals the potential applications of porcine plasma fibronectin that could be applied as a material for clinical wound healing and tissue repair.

Example 1. Materials and Cells

U2OS (human bone osteosarcoma cell line) and Hela (human cervical adenocarcinoma epithelial cell line) were gifts from Prof. R.-H. Chen's laboratory (Academia Sinica, Taipei, Taiwan) and were maintained in DMEM-high glucose (Invitrogen) supplemented with 10% FBS (Invitrogen)

and 1% antibiotic solution (penicillin and streptomycin; Invitrogen) under 5% CO2. HFF1 (human foreskin fibroblasts) cells were purchased from ATCC and were maintained in DMEM-high glucose supplemented with 15% FBS and 1% antibiotic solution (penicillin and streptomycin) under 5% CO2. The homo plasma was obtained from human blood donated by blood donors. All methods related to human blood were carried out in accordance with relevant guidelines and regulations. All experiments protocols related to human blood were approved by the Ethics Committee of the Institutional Review Board (IRB) of National Yang-Ming University. Informed consent was obtained from all subjects. The porcine plasma was obtained from CHAIS-HAN FOODS CO., LTD.

Example 2. Plasma Fibronectin Preparation Procedure

Plasma Fibronectin Purification

This invent provides a method for purify the glycosylation fibronectin from porcine, comprising: step 1, cleared plasma was passed through a pre-column of gelatin-Sepharose Fast Flow 4B; step 2, removing nonspecifically adsorbed proteins to the gel with sequential washing with TBS-EDTA 50 ml; step 3, removing nonspecifically adsorbed proteins to the gel with sequential washing with 1 M NaCl 50 ml; step 4, removing nonspecifically adsorbed proteins to the gel with sequential washing with <0.5 M Arginine (Arg) 50 ml; step 5, eluting fibronectin sample with >0.5M Arg; step 6, dialyzing fibronectin sample with TBS (pH 5-8) for 24 hours at 4° C.; step 7, concentrating fibronectin sample by Vivaspin 20 centrifugal concentrator (Molecular Weight Cut Off: 100 kDa).

Result

Figure 1:
FIG. 1 shows the purification method.
Figure 1:
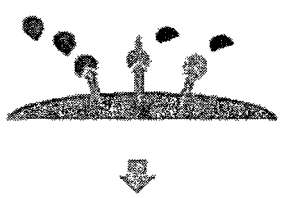
Figure 1:
Figure 1:
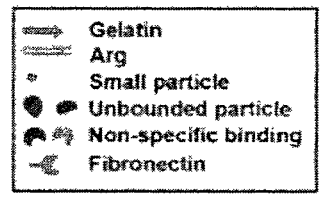
Figure 2:
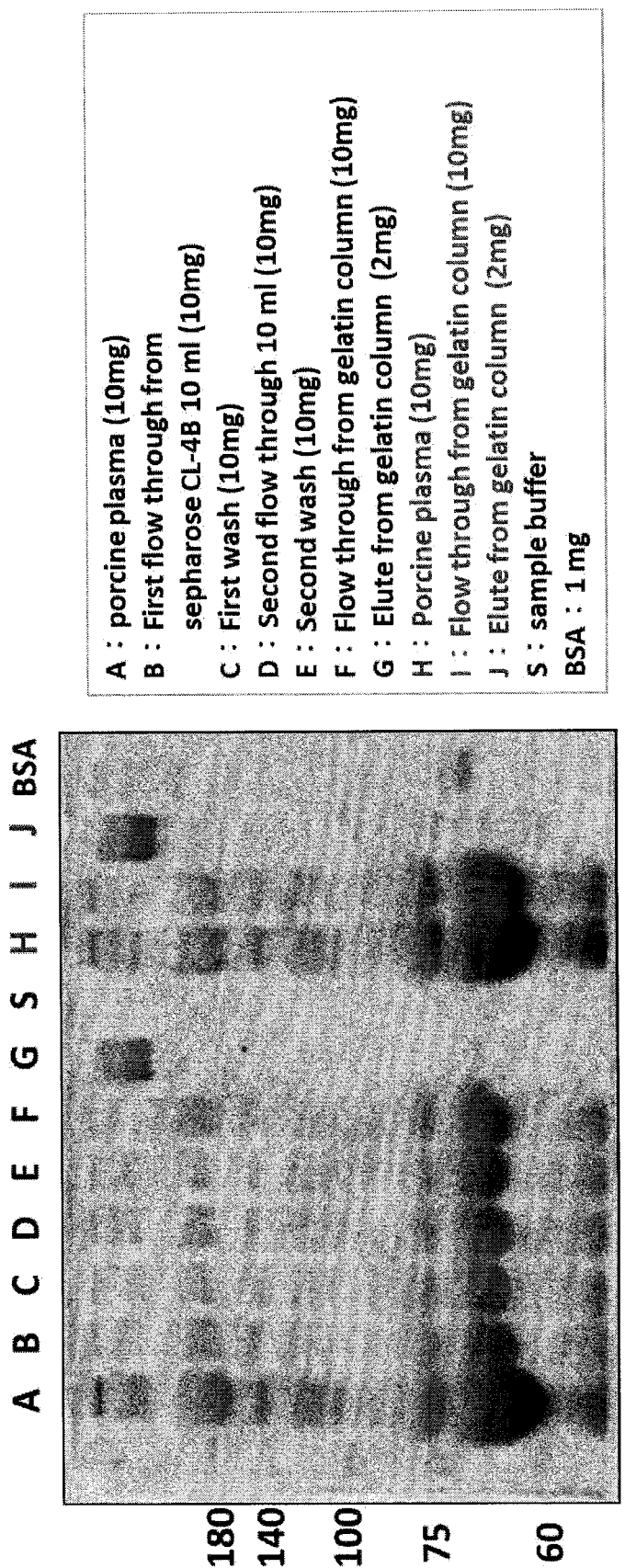
FIG. 2 shows the fractions of the washed materials and eluted materials that obtained from the gelatin-Sepharose Fast Flow 4B column.

This invention used a plasma fibronectin purification method to isolate high quality fibronectin proteins with glycans preservation from porcine plasma. Plasma was loaded into a pre-column of gelatin-Sepharose Fast Flow 4B. The gel was washed sequentially with TBS-EDTA, 1 M NaCl and <0.5 M Arginine (Arg) to remove non-specific binding proteins, leaving bound fibronectin for elution with >0.5 M Arg. The fractions of eluted fibronectin were pooled and dialyzed in TBS for 48 h at 4° C. and concentrated by Vivaspin 20 centrifugal concentrator (Molecular Weight Cut Off: 100 kDa) (FIG. 1-2).

Plasma Fibronectin Modification

This invent provides a method to modify the glycosylated porcine fibronectin, comprising: step 1, preparing porcine plasma fibronectin (1 mg) in buffer (pH 5~7); step 2, adding 5~50 units α2-3,6,8 Neuraminidase (One unit is defined as the amount of enzyme required to cleave>95% of the terminal α-Neu5Ac from 1 nmol Neu5Acα2-3Galβ1-3GlcNAcβ1-3Galβ1-4Glc-7-amino-4-methyl-coumarin (AMC), in 5 minutes at 37° C. in a total reaction volume of 10 µl; step 3, incubate for 1~24 hours in 37° C.

Glycopeptide Identification for Plasma Fibronectin

Precipitated fibronectin protein pellets (~10 µg) were subjected to protein digestion using a protocol with trypsin. The digested peptide mixtures were dissolved in 0.1% formic acid and then analyzed using a Dionex Ultimate 3000 nanoLC system (Thermo Scientific) interfaced to an Orbitrap Fusion Tribrid mass spectrometer (Thermo Scientific) equipped with a PicoView nanosprayer (New Objective). The peptides were loaded directly onto a 25 cm×75 µm C18 column (Acclaim PepMap® RSLC, Thermo Scientific) and separated using a 120-min linear gradient of 100% mobile phase A (0.1% formic acid in water) to 40% mobile phase B (acetonitrile with 0.1% formic acid) at a flow rate of 300 nL/min. The eluted peptides were detected in the positive ion mode using a nanospray source. The mass spectrometer was programmed in the data-dependent mode over 3 secs, which consisted of a cycle of one full-scan mass spectrum (400-2000 m/z) on the Orbitrap scan with 120,000 resolution at m/z 400 and an automatic gain control (AGC) target at 200,000 followed by quadrupole isolation with higherenergy collisional dissociation (HCD) MS2 at a normalized collision energy of 30%. HCD MS2 fragment ions detected in the Orbitrap analyzer at 30,000 resolution (AGC target at 100,000) with any previously selected ions dynamically excluded for 60 s. For the database search, the MS datasets for homo and porcine plasma fibronectin were performed using the Byonic™ search energy (Protein Metrics, v.2.7.4) against FN1_human or FN1_Sus scrofa from the Swiss Prot (Swiss Institute of Bioinformatics) database, respectively. Protein modifications were set as carbamidomethyl (C) (fixed), deamidated (N) (variable), oxidation (M) (variable) and N-glycan modifications (182 in homo N-Glycan database; 309 in mammalian N-Glycan database). Up to two missed cleavage was allowed. The mass tolerance was set as ±5 ppm for the MS spectra and ±10 ppm for the MS/MS spectra. For glycopeptide identification, the Byonic score was over 100 and the false discovery rate (FDR) was less than 1%.

Result

Figure 3:
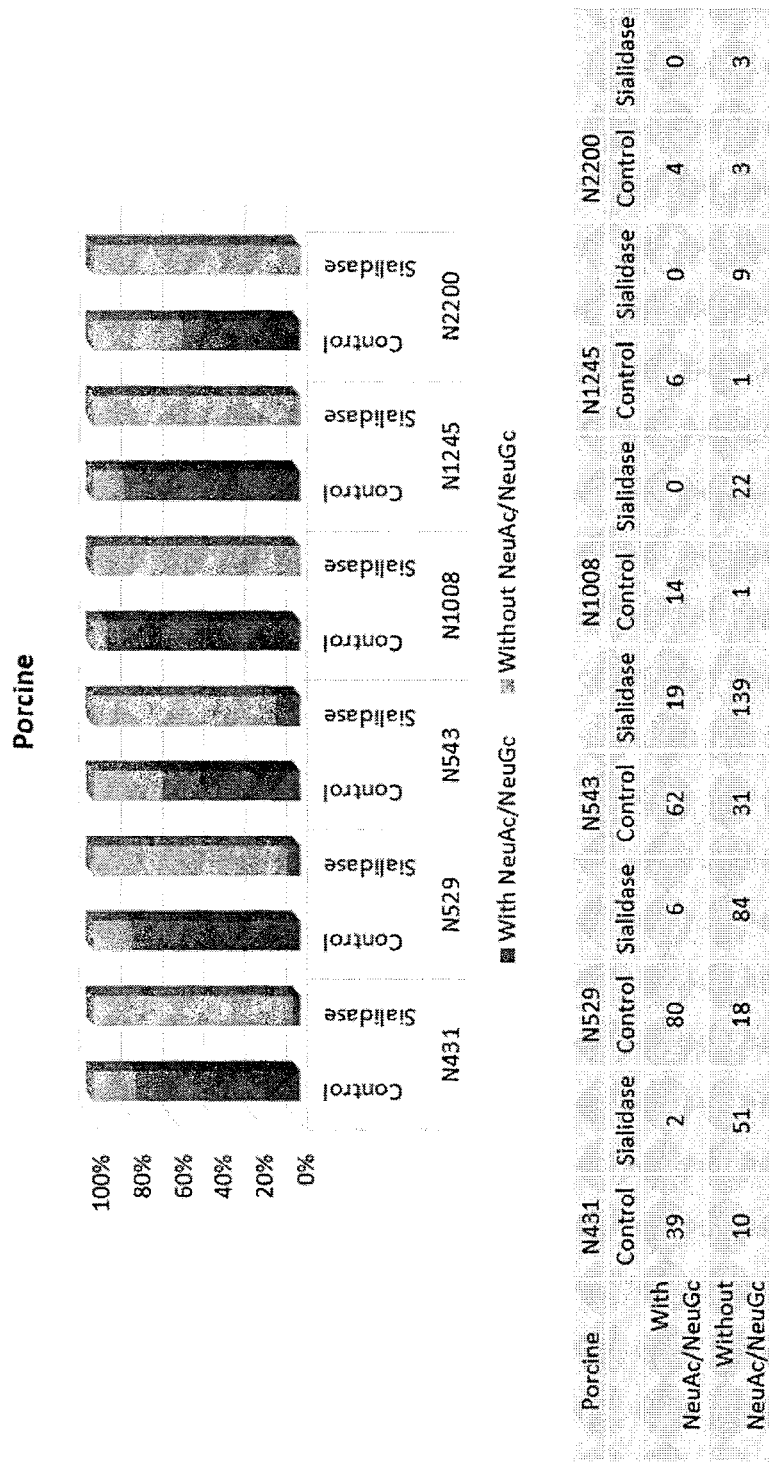
FIG. 3 shows the percentage of the spectral counts of the glycans with or without sialic acids (Neu5Ac or Neu5GC) relative to the total spectral counts for individual detected N-glycosylation sites.

This invention used α2-3,6,8 Neuraminidase to remove N-acetylneuraminic acid (Neu5Ac) and N-glycolyl-neuraminic acid (Neu5GC) residues on the porcine fibronectin. The results showed that the porcine fibronectin after modification could be used in wound healing and play the same function as homo fibronectin (FIG. 3).

Example 3. Homo and Porcine Plasma Fibronectin Show Comparable Effects in Terms of Cell Adhesion and Migration Wound Healing Analysis U2OS, Hela or HFF1 cells growing on tissue culture plates were trypsinized and re-seeded on 10 µg/ml fibronectin-coated 6-well plates in the culture medium for 16 h and then placed in the temperature-controlled and CO2-controlled chamber of a microscope (Axio Observer.Z1, Zeiss) equipped with a 10×0.25 NA objective lens (Zeiss). Time-lapse images were obtained at 15-min intervals over 12 h using an AxioCamMR3 CCD camera operated by the Zen image analysis software (Zeiss). To calculate the percentage of wound closure, the wound area over a 6-h period or a 12-h period of migration was obtained from the time-lapse movies using the Metamorph image analysis software (Molecular Device), and calculated as the ratio of net wound-healing area to the wound area at 0-h after wounding.

Result

Figure 4A:
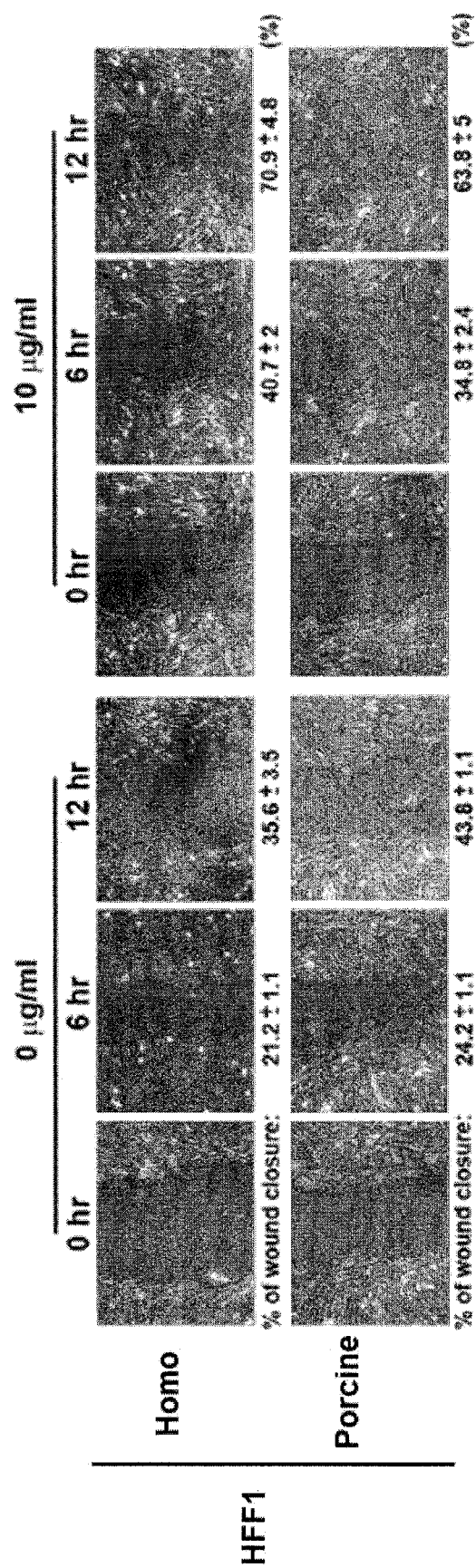
FIG. 4a-c shows the isolated homo and porcine fibronectin proteins exhibited similar wound closure effect using U2OS, HFF1 and Hela cells.
Figure 4B:
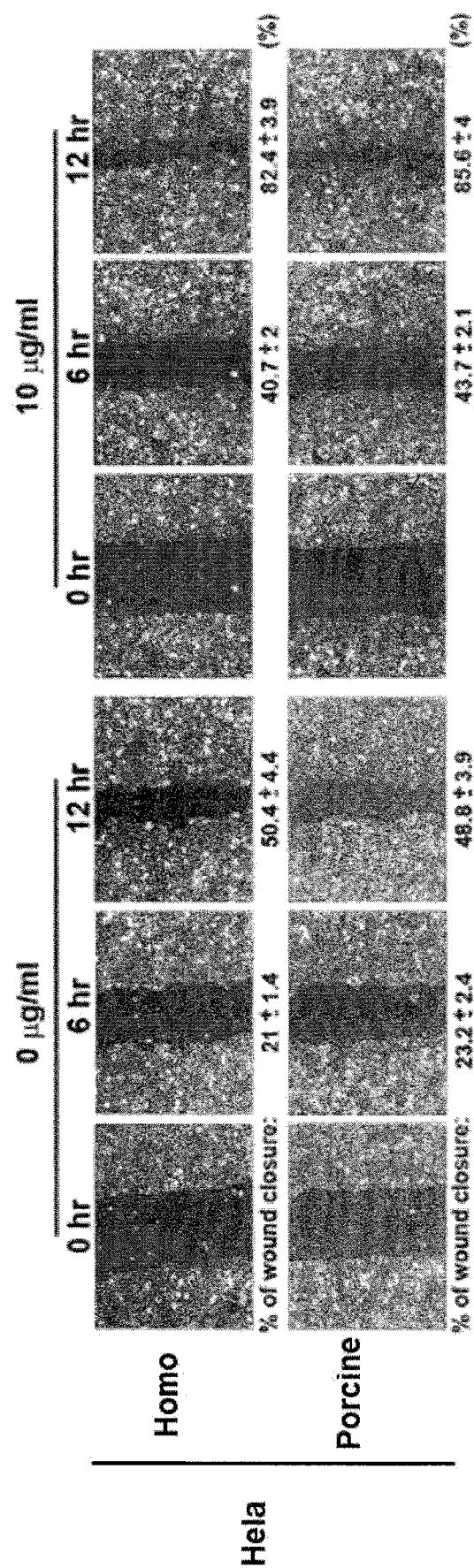
Figure 4C:
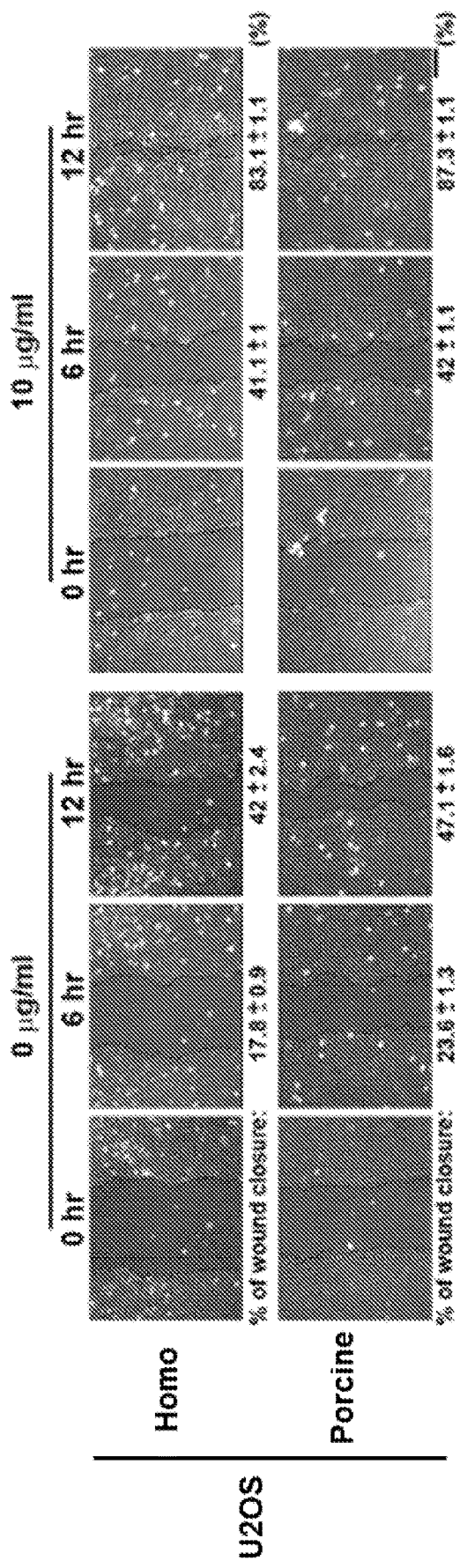

To compare the functionalities of the isolated fibronectin from homo and porcine plasma, we carried out wound-healing migration assays using cells that had been plated on the fibronectin-coated plates. This revealed that the isolated homo and porcine fibronectin proteins exhibited similar wound closure effect using U2OS, HFF1 and Hela cells (FIG. 4a-c). Therefore, homo and porcine fibronectins would seem to possess comparable capabilities in terms of regulating cell migration.

Adhesion Assay

The cell adhesion assays used 96-well plates that had been pretreated with 1% denatured BSA at 37° C. for 1 h and then coated with the indicated concentration of homo or porcine plasma fibronectin. To perform the experiments, U2OS cells growing on tissue culture plates were trypsinized, re-suspended in serum-free medium and then re-seeded on the pre-treated 96-well plates for 10 min or overnight (~16 h). After incubation, any non-attached cells were removed completely by washing with PBS twice, and adherent cells were fixed with 5% glutaldehyde in $H_2O$ for 25 min at room temperature, flowed by staining with 0.1% crystal violet in $H_2O$ for 25 min at room temperature. After removing any un-bound crystal violet, the crystal violet-labelled adherent cells were solubilized in 50 μl solution A (50% ethanol and 0.1% acetic acid in $H_2O$), and the amount of crystal violet present measured using a Thermo Scientific Multiskan Spectrum at OD 550 nm. The results are presented graphically using Excel software (Microsoft).

Immunofluorescence Staining and Image Analysis

For paxillin staining, the cells were fixed and immunostained using a method previously described. For TIRFM imaging, the cells were mounted on slides with PBS containing N-propyl gallate. TIRFM images were obtained using 100×1.49NA (Oil-Immersion) Plan objective lens (Nikon) using the iLas multi-modal of the TIRF (Roper)/ spinning disk confocal (CSUX1, Yokogawa) microscope system equipped with an Evolve EMCCD camera (Photometrics). To determine the adhesion area, TIRFM images of paxillin-stained cells were thresholded to highlight only the FAs and the areas of these regions were recorded using Metamorph. The total area of recorded FAs was summed to give the adhesion area. The results are presented graphically using Excel software (Microsoft).

Cell Spreading Assay and Image Analysis

Cells growing on tissue culture plates were trypsinized and re-seeded on plates coated with the indicated concentration of homo or porcine plasma fibronectin to allow them to adhere and spread (30 min). Next the cells were fixed with 4% paraformaldehyde in PBS for 20 min at room temperature and then imaged using a microscope 22 (Eclipse TS100; Nikon) coupled with a 20×0.45NA objective lens (Nikon) and a WHITE CCD camera operated by ISCapture software (TUCSEN). To calculate the cell spreading area, the cell area was manually circled on the phase images using Metamorph image analysis software (Molecular Device) and the results are presented graphically using Excel software (Microsoft).

Result

Figure 5:
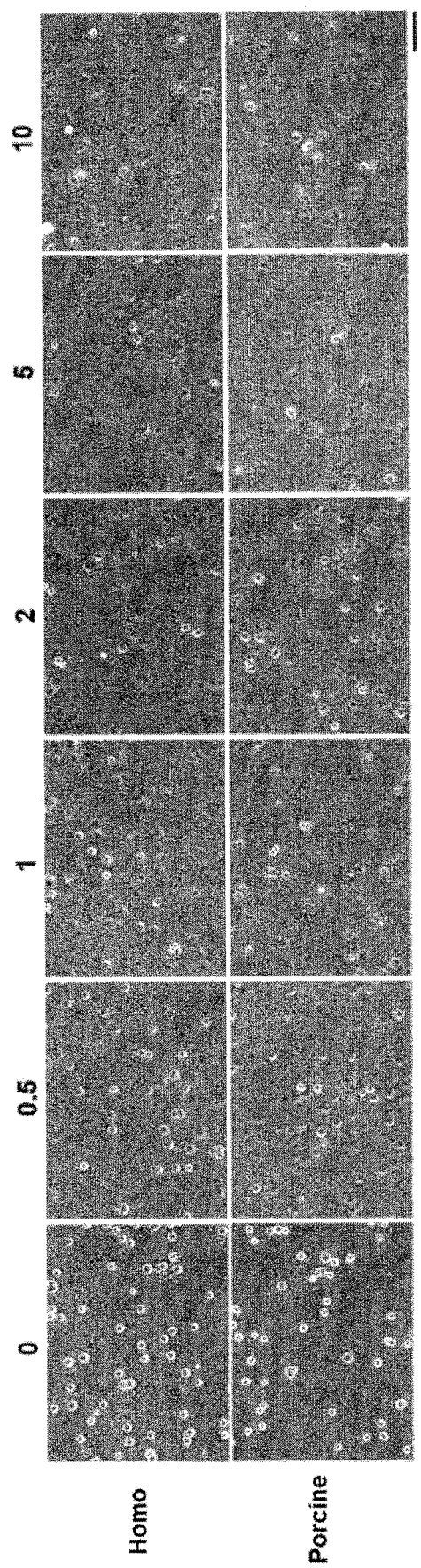
FIG. 5 shows U2OS cells were plated on coverslips coated with the indicated fibronectin concentration (µg/ml) for 30 min and then the images were taken by phase contrast microscopy. Bar, 100 µm.
Figure 6:
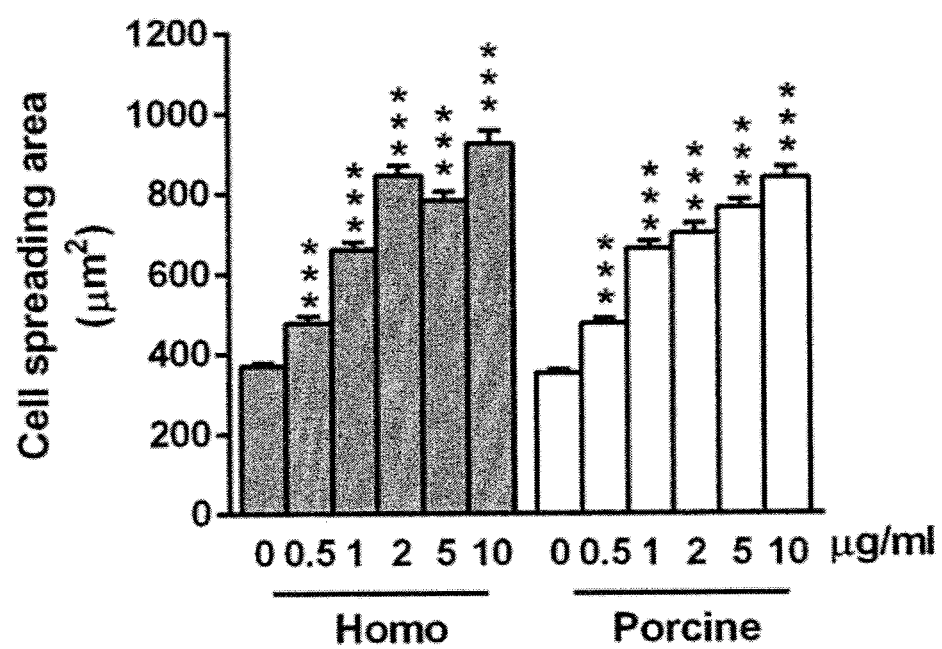
FIG. 6 shows the area of cells spreading on coverslips coated with the indicated fibronectin concentration (µg/ml).
Figure 7:
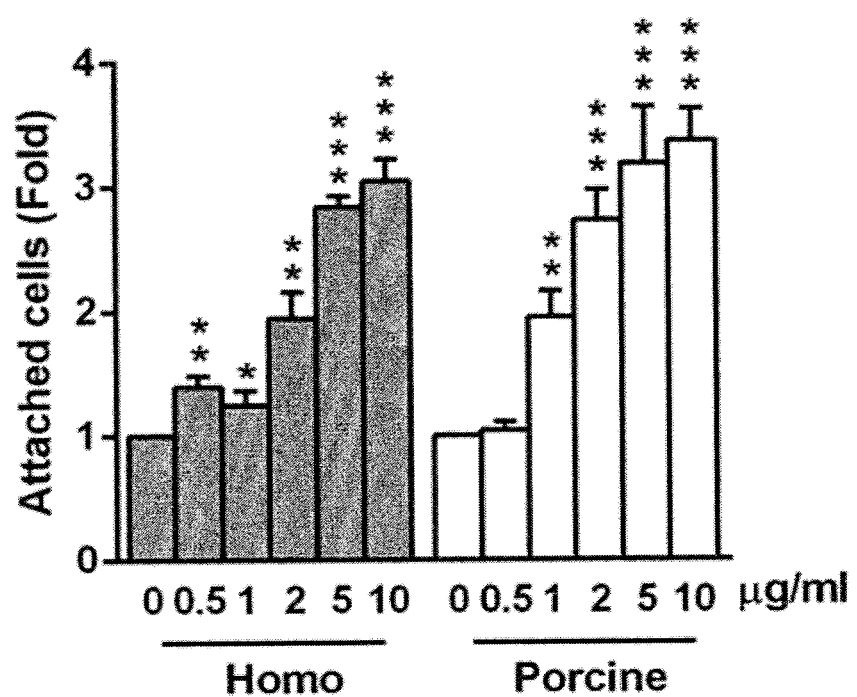
FIG. 7 shows U2OS cells were plated on the indicated concentration of fibronectin for 30 min and then their cell attachment was measured. Fold of cells remaining attached on the indicated concentration of fibronectin relative to that on 0 µg/ml fibronectin.
Figure 8:
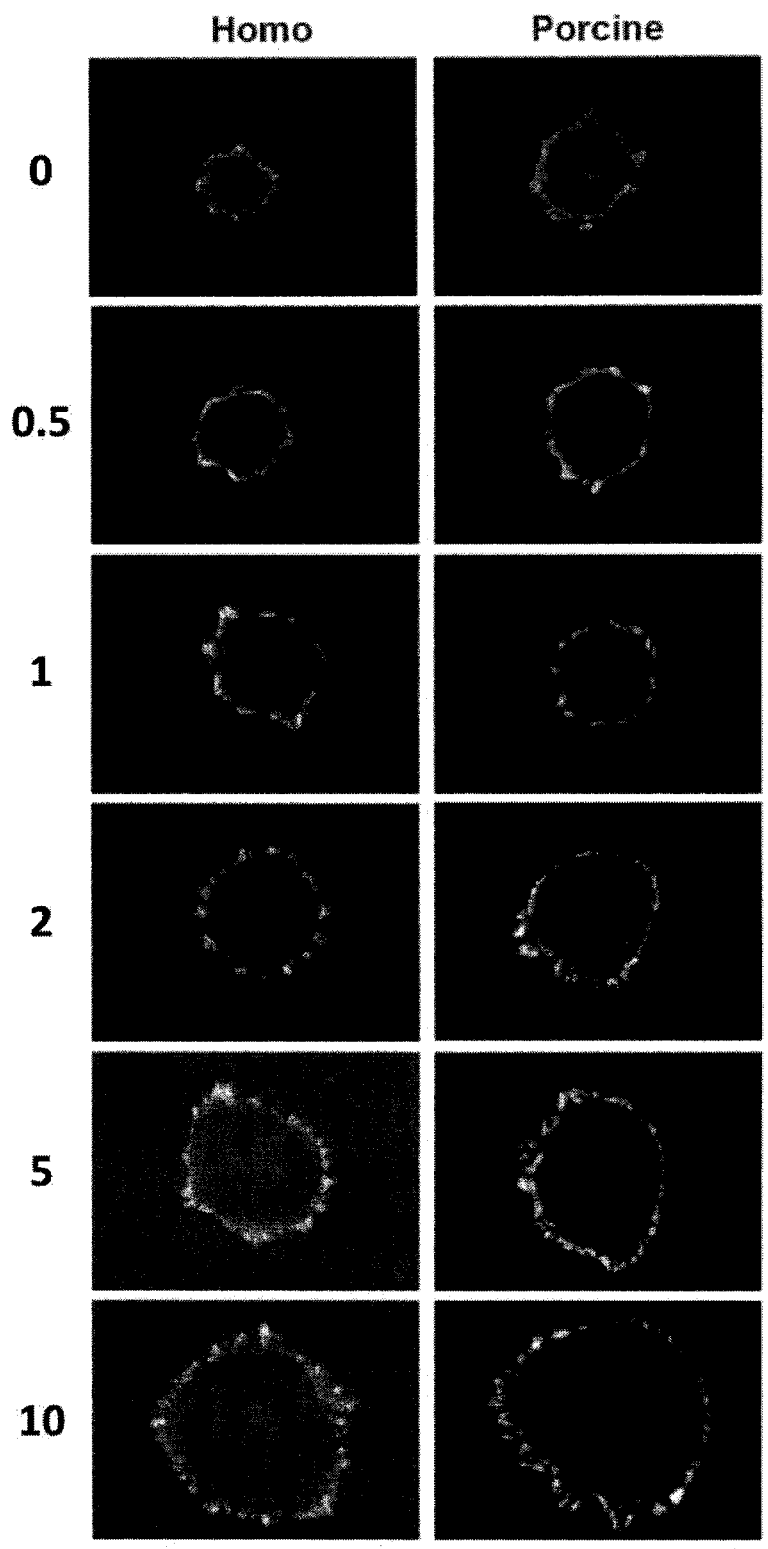
FIG. 8 shows TIRFM images of U2OS cells that had been plated for 1.5 h on coverslips coated with the indicated fibronectin concentration and immunostained with paxillin. Bar, 10 µm.
Figure 9:
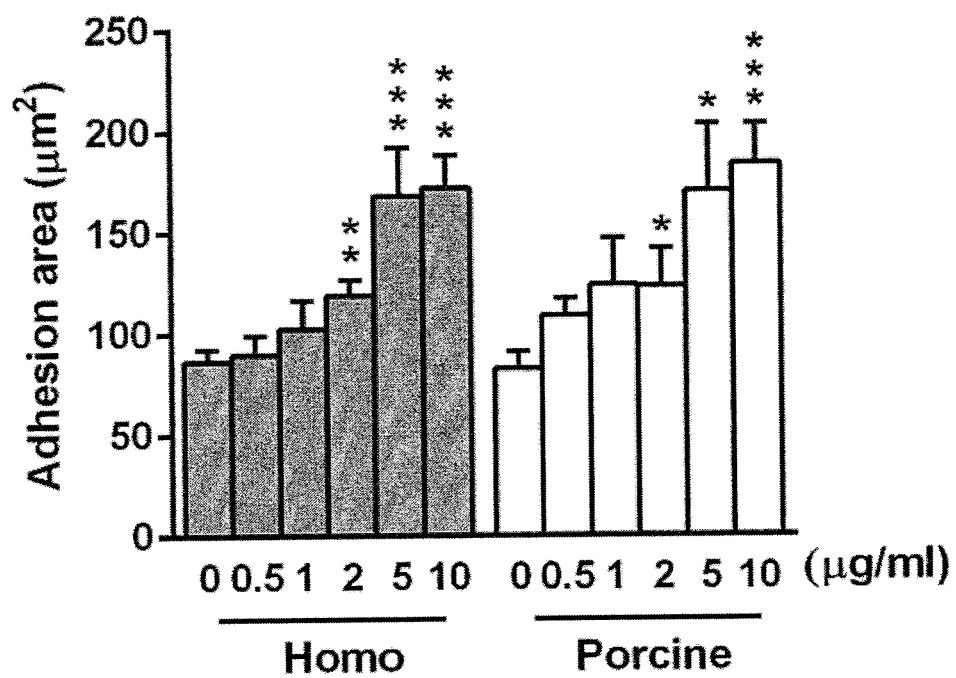
FIG. 9 shows the sum of the total area of paxillin-marked focal adhesions within a cell versus the fibronectin concentration.

To determine whether homo and porcine fibronectins are comparable when regulating adhesion strength, we initially compared the effect of homo and porcine fibronectin on cell spreading and adhesion. The area of cell spreading was measured after 30 min using U2OS cells that had been seeded onto plates coated with increasing concentrations of homo or porcine fibronectin (FIG. 5). The results revealed that the area of cell spreading increased as the concentration of fibronectin increased for both fibronectins (FIG. 6). Cell adhesive capacity was also quantified and this revealed that increasing concentrations of homo or porcine fibronectin promoted cell adherence to fibronectin (FIG. 7). Next, we immunolabelled and visualized the cellular pattern of the FA marker paxillin (FIG. 8) using cells seeded on increasing concentration of homo or porcine fibronectin for 1.5 h. The results showed an increased area of adhesion ($\mu m^2$) as the concentration of each fibronectin increased; the quantification was in terms of the area of paxillin-marked adhesion (FIG. 9).

Figure 10:
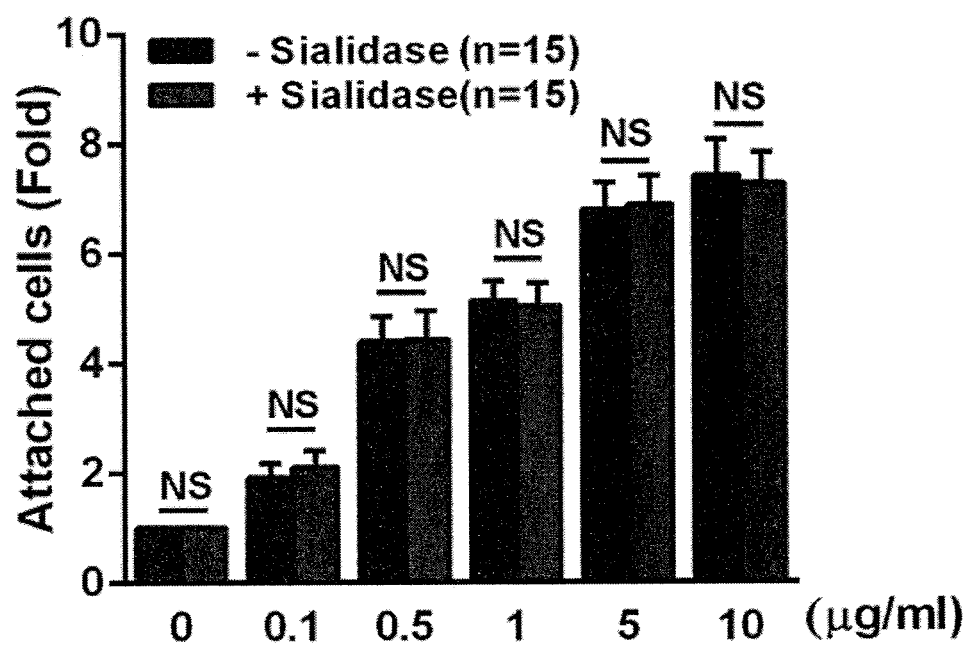
FIG. 10 shows the removal of sialic acids from porcine fibronectin did not affect the cell-fibronectin association.

To further determine whether sialic acids (Neu5Ac and Neu5GC) on fibronectin do not responsible for the functioning of fibronectin during adhesion enhancement, we first used α2-3,6,8 Neuraminidase (sialidase) to cleave sialic acids from porcine fibronectin (FIG. 3). We found that the removal of sialic acids from porcine fibronectin did not affect the cell-fibronectin association (FIG. 10). Therefore, the sialic acid-trimming glycosylated fibronectin can be used in for novel wound dressing materials in clinical application to enhance wound healing without the possibility of an aberrant immune response caused by the presence of Neu5Gc.

Example 4. Porcine Plasma Fibronectin Shows Better Effects in Wound Closure After Proteinase Digestion MMP3 Digestion of Porcine Plasma Fibronectin To have better exposure the glycan structures on porcine fibronectin for better wound closure function. This invent provide a method for modify the glycosylated porcine fibronectin, comprising: incubating porcine plasma fibronectin with MMP3 overnight at 37° C. at an enzyme-substrate ratio from 1:5 to 1:30.

Wound Healing Analysis

U2OS cells growing on tissue culture plates were trypsinized and re-seeded on 10 μg/ml fibronectin or digested fibronectin-coated 6-well plates in the culture medium for 16 h and then placed in the temperature-controlled and CO2-controlled chamber of a microscope (Axio Observer.Z1, Zeiss) equipped with a 10×0.25 NA objective lens (Zeiss). Time-lapse images were obtained at 15-min intervals over 12 h using an AxioCamMR3 CCD camera operated by the Zen image analysis software (Zeiss). To calculate the percentage of wound closure, the wound area over a 12-h period of migration was obtained from the time-lapse movies using the Metamorph image analysis software (Molecular Device), and calculated as the ratio of net wound-healing area to the wound area at 0-h after wounding.

Result

Figure 11:
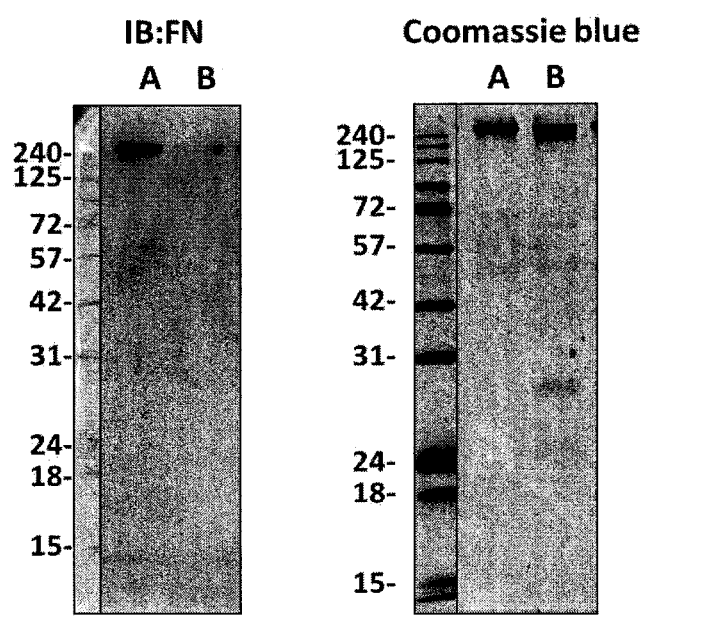
FIG. 11 shows the MMP3 digestion of porcine fibronectin result.
Figure 12:
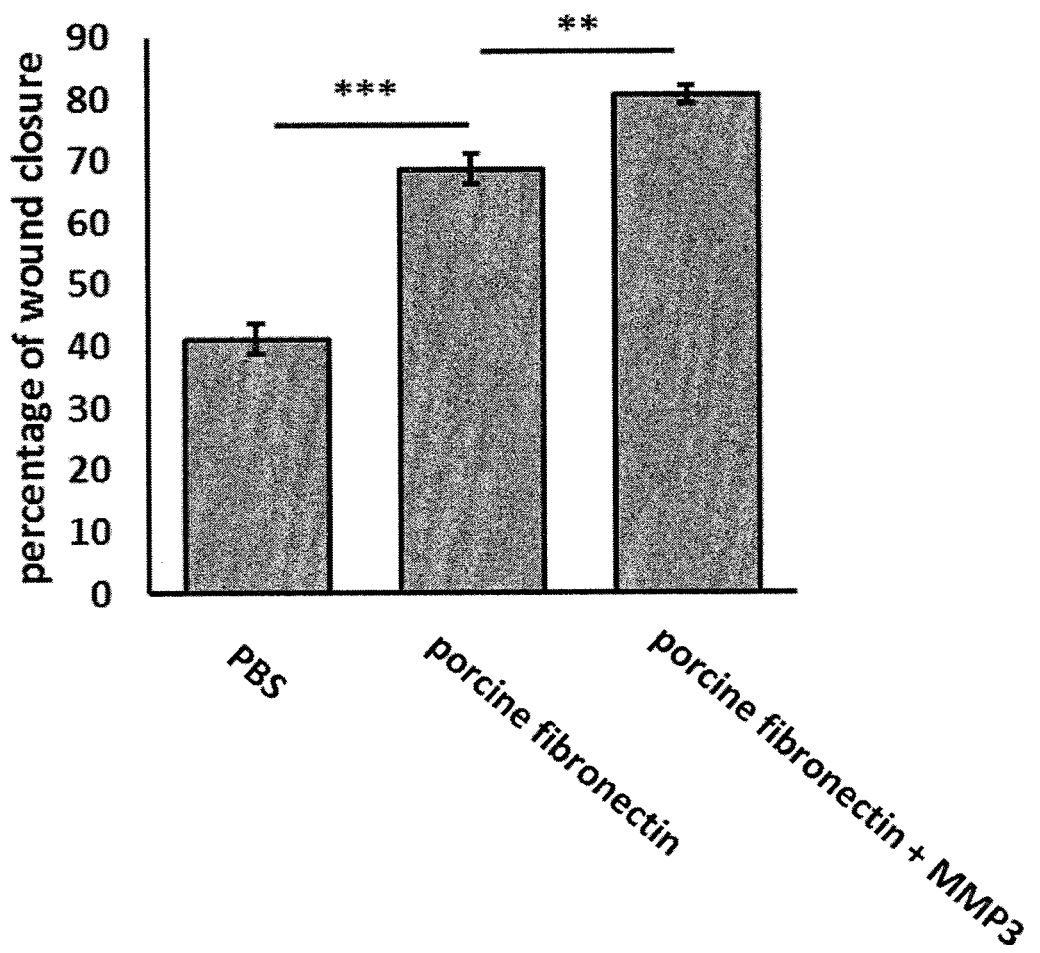
FIG. 12 shows percentage of wound closure by treating with porcine fibronectin or porcine fibronectin with MMP3.

This invention used MMP3 to generate porcine fibronectin peptides (FIG. 11). To compare the effect of digested fibronectin peptides and non-digested fibronectin, we carried out wound-healing migration assays using cells that had been plated on the digested fibronectin peptides- or non-digested fibronectin-coated plates. This revealed that digested fibronectin peptides significantly promote wound closure effect (FIG. 12). Therefore, the fibronectin peptides possess enhanced ability in terms of regulating cell migration.

What is claimed is:

1. A method for enhanced wound healing in a subject, wherein the method comprises:
   a) treating porcine fibronectin with an enzyme that modifies the glycans attached to the fibronectin protein, thereby producing a porcine fibronectin with modified glycans; and
   b) administering the porcine fibronectin with modified glycans to the subject.

2. The method according to claim 1, wherein the modified glycans are a plurality of sialic acid molecules.

3. The method according to claim 2, wherein the plurality of sialic acid molecules comprise N-acetylneuraminic acid (Neu5Ac) and/or N-glycolylneuraminic acid (Neu5GC) residues.

4. The method according to claim 2, wherein the plurality of sialic acid molecules are removed.

5. The method according to claim 1, wherein the enzyme is the α2-3,6,8 Neuraminidase.

6. The method according to claim 5, wherein the enzyme further comprises a proteinase with ability to digest fibronectin.

7. The method according to claim 6, wherein the proteinase is the matrix metalloproteinase 3.

8. The method according to claim 1, wherein step a) is preceded by a step comprising isolating porcine fibronectin on an affinity column with a buffer under conditions that preserve the attachment of the glycans to the fibronectin protein.

* * * * *

SEQUENCE LISTING

<160> NUMBER OF SEQ ID NOS: 2

<210> SEQ ID NO 1
<211> LENGTH: 2477
<212> TYPE: PRT
<213> ORGANISM: Homo sapiens

<400> SEQUENCE: 1

```
Met Leu Arg Gly Pro Gly Pro Leu Leu Leu Ala Val Gln Cys
1               5                   10                  15

Leu Gly Thr Ala Val Pro Ser Thr Gly Ala Ser Lys Ser Lys Arg Gln
                20                  25                  30

Ala Gln Gln Met Val Gln Pro Gln Ser Pro Val Ala Val Ser Gln Ser
                35                  40                  45

Lys Pro Gly Cys Tyr Asp Asn Gly Lys His Tyr Gln Ile Asn Gln Gln
            50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
                100                 105                 110

Glu Arg Pro Lys Asp Ser Met Ile Trp Asp Cys Thr Cys Ile Gly Ala
                115                 120                 125

Gly Arg Gly Arg Ile Ser Cys Thr Ile Ala Asn Arg Cys His Glu Gly
130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
                180                 185                 190

Thr Ser Tyr Val Val Gly Glu Thr Trp Glu Lys Pro Tyr Gln Gly Trp
                195                 200                 205

Met Met Val Asp Cys Thr Cys Leu Gly Glu Gly Ser Gly Arg Ile Thr
210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
                260                 265                 270

His Thr Ser Val Gln Thr Thr Ser Ser Gly Ser Gly Pro Phe Thr Asp
                275                 280                 285

Val Arg Ala Ala Val Tyr Gln Pro Gln Pro His Pro Gln Pro Pro Pro
                290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
                340                 345                 350

Gly Asn Ser Asn Gly Glu Pro Cys Val Leu Pro Phe Thr Tyr Asn Gly
                355                 360                 365

Arg Thr Phe Tyr Ser Cys Thr Thr Glu Gly Arg Gln Asp Gly His Leu
                370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                405                 410                 415
```

-continued

Gly Ala Leu Cys His Phe Pro Phe Leu Tyr Asn Asn His Asn Tyr Thr
                420                 425                 430

Asp Cys Thr Ser Glu Gly Arg Arg Asp Asn Met Lys Trp Cys Gly Thr
            435                 440                 445

Thr Gln Asn Tyr Asp Ala Asp Gln Lys Phe Gly Phe Cys Pro Met Ala
        450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
        515                 520                 525

Asp Thr Phe His Lys Arg His Glu Glu Gly His Met Leu Asn Cys Thr
    530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
        595                 600                 605

Ser Gly Pro Val Glu Val Phe Ile Thr Glu Thr Pro Ser Gln Pro Asn
    610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
            660                 665                 670

Pro Gly Val Val Tyr Glu Gly Gln Leu Ile Ser Ile Gln Gln Tyr Gly
        675                 680                 685

His Gln Glu Val Thr Arg Phe Asp Phe Thr Thr Thr Ser Thr Ser Thr
    690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
            740                 745                 750

Glu Tyr Glu Leu Ser Glu Glu Gly Asp Glu Pro Gln Tyr Leu Asp Leu
        755                 760                 765

Pro Ser Thr Ala Thr Ser Val Asn Ile Pro Asp Leu Leu Pro Gly Arg
    770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Thr Thr Val Asp Gln Val Asp Asp Thr Ser Ile Val Val Arg Trp Ser
            820                 825                 830

-continued

Arg Pro Gln Ala Pro Ile Thr Gly Tyr Arg Ile Val Tyr Ser Pro Ser
            835                 840                 845

Val Glu Gly Ser Ser Thr Glu Leu Asn Leu Pro Glu Thr Ala Asn Ser
    850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
            915                 920                 925

Pro Pro Glu Ser Ala Val Thr Gly Tyr Arg Val Asp Val Ile Pro Val
            930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
            980                 985                 990

Gln Thr Thr Lys Leu Asp Ala Pro Thr Asn Leu Gln Phe Val Asn Glu
            995                 1000                1005

Thr Asp Ser Thr Val Leu Val Arg Trp Thr Pro Pro Arg Ala Gln
    1010                1015                1020

Ile Thr Gly Tyr Arg Leu Thr Val Gly Leu Thr Arg Arg Gly Gln
    1025                1030                1035

Pro Arg Gln Tyr Asn Val Gly Pro Ser Val Ser Lys Tyr Pro Leu
    1040                1045                1050

Arg Asn Leu Gln Pro Ala Ser Glu Tyr Thr Val Ser Leu Val Ala
    1055                1060                1065

Ile Lys Gly Asn Gln Glu Ser Pro Lys Ala Thr Gly Val Phe Thr
    1070                1075                1080

Thr Leu Gln Pro Gly Ser Ser Ile Pro Pro Tyr Asn Thr Glu Val
    1085                1090                1095

Thr Glu Thr Thr Ile Val Ile Thr Trp Thr Pro Ala Pro Arg Ile
    1100                1105                1110

Gly Phe Lys Leu Gly Val Arg Pro Ser Gln Gly Gly Glu Ala Pro
    1115                1120                1125

Arg Glu Val Thr Ser Asp Ser Gly Ser Ile Val Val Ser Gly Leu
    1130                1135                1140

Thr Pro Gly Val Glu Tyr Val Tyr Thr Ile Gln Val Leu Arg Asp
    1145                1150                1155

Gly Gln Glu Arg Asp Ala Pro Ile Val Asn Lys Val Val Thr Pro
    1160                1165                1170

Leu Ser Pro Pro Thr Asn Leu His Leu Glu Ala Asn Pro Asp Thr
    1175                1180                1185

Gly Val Leu Thr Val Ser Trp Glu Arg Ser Thr Thr Pro Asp Ile
    1190                1195                1200

Thr Gly Tyr Arg Ile Thr Thr Thr Pro Thr Asn Gly Gln Gln Gly
    1205                1210                1215

Asn Ser Leu Glu Glu Val Val His Ala Asp Gln Ser Ser Cys Thr
    1220                1225                1230

```
Phe Asp Asn Leu Ser Pro Gly Leu Glu Tyr Asn Val Ser Val Tyr
1235                1240                1245

Thr Val Lys Asp Asp Lys Glu Ser Val Pro Ile Ser Asp Thr Ile
1250                1255                1260

Ile Pro Glu Val Pro Gln Leu Thr Asp Leu Ser Phe Val Asp Ile
1265                1270                1275

Thr Asp Ser Ser Ile Gly Leu Arg Trp Thr Pro Leu Asn Ser Ser
1280                1285                1290

Thr Ile Ile Gly Tyr Arg Ile Thr Val Val Ala Ala Gly Glu Gly
1295                1300                1305

Ile Pro Ile Phe Glu Asp Phe Val Asp Ser Ser Val Gly Tyr Tyr
1310                1315                1320

Thr Val Thr Gly Leu Glu Pro Gly Ile Asp Tyr Asp Ile Ser Val
1325                1330                1335

Ile Thr Leu Ile Asn Gly Gly Glu Ser Ala Pro Thr Thr Leu Thr
1340                1345                1350

Gln Gln Thr Ala Val Pro Pro Thr Asp Leu Arg Phe Thr Asn
1355                1360                1365

Ile Gly Pro Asp Thr Met Arg Val Thr Trp Ala Pro Pro Pro Ser
1370                1375                1380

Ile Asp Leu Thr Asn Phe Leu Val Arg Tyr Ser Pro Val Lys Asn
1385                1390                1395

Glu Glu Asp Val Ala Glu Leu Ser Ile Ser Pro Ser Asp Asn Ala
1400                1405                1410

Val Val Leu Thr Asn Leu Leu Pro Gly Thr Glu Tyr Val Val Ser
1415                1420                1425

Val Ser Ser Val Tyr Glu Gln His Glu Ser Thr Pro Leu Arg Gly
1430                1435                1440

Arg Gln Lys Thr Gly Leu Asp Ser Pro Thr Gly Ile Asp Phe Ser
1445                1450                1455

Asp Ile Thr Ala Asn Ser Phe Thr Val His Trp Ile Ala Pro Arg
1460                1465                1470

Ala Thr Ile Thr Gly Tyr Arg Ile Arg His His Pro Glu His Phe
1475                1480                1485

Ser Gly Arg Pro Arg Glu Asp Arg Val Pro His Ser Arg Asn Ser
1490                1495                1500

Ile Thr Leu Thr Asn Leu Thr Pro Gly Thr Glu Tyr Val Val Ser
1505                1510                1515

Ile Val Ala Leu Asn Gly Arg Glu Glu Ser Pro Leu Leu Ile Gly
1520                1525                1530

Gln Gln Ser Thr Val Ser Asp Val Pro Arg Asp Leu Glu Val Val
1535                1540                1545

Ala Ala Thr Pro Thr Ser Leu Leu Ile Ser Trp Asp Ala Pro Ala
1550                1555                1560

Val Thr Val Arg Tyr Tyr Arg Ile Thr Tyr Gly Glu Thr Gly Gly
1565                1570                1575

Asn Ser Pro Val Gln Glu Phe Thr Val Pro Gly Ser Lys Ser Thr
1580                1585                1590

Ala Thr Ile Ser Gly Leu Lys Pro Gly Val Asp Tyr Thr Ile Thr
1595                1600                1605

Val Tyr Ala Val Thr Gly Arg Gly Asp Ser Pro Ala Ser Ser Lys
1610                1615                1620
```

```
Pro Ile Ser Ile Asn Tyr Arg Thr Glu Ile Asp Lys Pro Ser Gln
1625                1630                1635

Met Gln Val Thr Asp Val Gln Asp Asn Ser Ile Ser Val Lys Trp
1640                1645                1650

Leu Pro Ser Ser Ser Pro Val Thr Gly Tyr Arg Val Thr Thr Thr
1655                1660                1665

Pro Lys Asn Gly Pro Gly Pro Thr Lys Thr Lys Thr Ala Gly Pro
1670                1675                1680

Asp Gln Thr Glu Met Thr Ile Glu Gly Leu Gln Pro Thr Val Glu
1685                1690                1695

Tyr Val Val Ser Val Tyr Ala Gln Asn Pro Ser Gly Glu Ser Gln
1700                1705                1710

Pro Leu Val Gln Thr Ala Val Thr Asn Ile Asp Arg Pro Lys Gly
1715                1720                1725

Leu Ala Phe Thr Asp Val Asp Val Asp Ser Ile Lys Ile Ala Trp
1730                1735                1740

Glu Ser Pro Gln Gly Gln Val Ser Arg Tyr Arg Val Thr Tyr Ser
1745                1750                1755

Ser Pro Glu Asp Gly Ile His Glu Leu Phe Pro Ala Pro Asp Gly
1760                1765                1770

Glu Glu Asp Thr Ala Glu Leu Gln Gly Leu Arg Pro Gly Ser Glu
1775                1780                1785

Tyr Thr Val Ser Val Val Ala Leu His Asp Asp Met Glu Ser Gln
1790                1795                1800

Pro Leu Ile Gly Thr Gln Ser Thr Ala Ile Pro Ala Pro Thr Asp
1805                1810                1815

Leu Lys Phe Thr Gln Val Thr Pro Thr Ser Leu Ser Ala Gln Trp
1820                1825                1830

Thr Pro Pro Asn Val Gln Leu Thr Gly Tyr Arg Val Arg Val Thr
1835                1840                1845

Pro Lys Glu Lys Thr Gly Pro Met Lys Glu Ile Asn Leu Ala Pro
1850                1855                1860

Asp Ser Ser Ser Val Val Val Ser Gly Leu Met Val Ala Thr Lys
1865                1870                1875

Tyr Glu Val Ser Val Tyr Ala Leu Lys Asp Thr Leu Thr Ser Arg
1880                1885                1890

Pro Ala Gln Gly Val Val Thr Thr Leu Glu Asn Val Ser Pro Pro
1895                1900                1905

Arg Arg Ala Arg Val Thr Asp Ala Thr Glu Thr Thr Ile Thr Ile
1910                1915                1920

Ser Trp Arg Thr Lys Thr Glu Thr Ile Thr Gly Phe Gln Val Asp
1925                1930                1935

Ala Val Pro Ala Asn Gly Gln Thr Pro Ile Gln Arg Thr Ile Lys
1940                1945                1950

Pro Asp Val Arg Ser Tyr Thr Ile Thr Gly Leu Gln Pro Gly Thr
1955                1960                1965

Asp Tyr Lys Ile Tyr Leu Tyr Thr Leu Asn Asp Asn Ala Arg Ser
1970                1975                1980

Ser Pro Val Val Ile Asp Ala Ser Thr Ala Ile Asp Ala Pro Ser
1985                1990                1995

Asn Leu Arg Phe Leu Ala Thr Thr Pro Asn Ser Leu Leu Val Ser
2000                2005                2010
```

-continued

Trp Gln Pro Pro Arg Ala Arg Ile Thr Gly Tyr Ile Ile Lys Tyr
2015                2020                2025

Glu Lys Pro Gly Ser Pro Pro Arg Glu Val Val Pro Arg Pro Arg
2030                2035                2040

Pro Gly Val Thr Glu Ala Thr Ile Thr Gly Leu Glu Pro Gly Thr
2045                2050                2055

Glu Tyr Thr Ile Tyr Val Ile Ala Leu Lys Asn Asn Gln Lys Ser
2060                2065                2070

Glu Pro Leu Ile Gly Arg Lys Lys Thr Asp Glu Leu Pro Gln Leu
2075                2080                2085

Val Thr Leu Pro His Pro Asn Leu His Gly Pro Glu Ile Leu Asp
2090                2095                2100

Val Pro Ser Thr Val Gln Lys Thr Pro Phe Val Thr His Pro Gly
2105                2110                2115

Tyr Asp Thr Gly Asn Gly Ile Gln Leu Pro Gly Thr Ser Gly Gln
2120                2125                2130

Gln Pro Ser Val Gly Gln Gln Met Ile Phe Glu Glu His Gly Phe
2135                2140                2145

Arg Arg Thr Thr Pro Pro Thr Thr Ala Thr Pro Ile Arg His Arg
2150                2155                2160

Pro Arg Pro Tyr Pro Pro Asn Val Gly Glu Glu Ile Gln Ile Gly
2165                2170                2175

His Ile Pro Arg Glu Asp Val Asp Tyr His Leu Tyr Pro His Gly
2180                2185                2190

Pro Gly Leu Asn Pro Asn Ala Ser Thr Gly Gln Glu Ala Leu Ser
2195                2200                2205

Gln Thr Thr Ile Ser Trp Ala Pro Phe Gln Asp Thr Ser Glu Tyr
2210                2215                2220

Ile Ile Ser Cys His Pro Val Gly Thr Asp Glu Glu Pro Leu Gln
2225                2230                2235

Phe Arg Val Pro Gly Thr Ser Thr Ser Ala Thr Leu Thr Gly Leu
2240                2245                2250

Thr Arg Gly Ala Thr Tyr Asn Val Ile Val Glu Ala Leu Lys Asp
2255                2260                2265

Gln Gln Arg His Lys Val Arg Glu Glu Val Val Thr Val Gly Asn
2270                2275                2280

Ser Val Asn Glu Gly Leu Asn Gln Pro Thr Asp Asp Ser Cys Phe
2285                2290                2295

Asp Pro Tyr Thr Val Ser His Tyr Ala Val Gly Asp Glu Trp Glu
2300                2305                2310

Arg Met Ser Glu Ser Gly Phe Lys Leu Leu Cys Gln Cys Leu Gly
2315                2320                2325

Phe Gly Ser Gly His Phe Arg Cys Asp Ser Ser Arg Trp Cys His
2330                2335                2340

Asp Asn Gly Val Asn Tyr Lys Ile Gly Glu Lys Trp Asp Arg Gln
2345                2350                2355

Gly Glu Asn Gly Gln Met Met Ser Cys Thr Cys Leu Gly Asn Gly
2360                2365                2370

Lys Gly Glu Phe Lys Cys Asp Pro His Glu Ala Thr Cys Tyr Asp
2375                2380                2385

Asp Gly Lys Thr Tyr His Val Gly Glu Gln Trp Gln Lys Glu Tyr
2390                2395                2400

-continued

Leu Gly Ala Ile Cys Ser Cys Thr Cys Phe Gly Gly Gln Arg Gly
    2405            2410            2415

Trp Arg Cys Asp Asn Cys Arg Arg Pro Gly Gly Glu Pro Ser Pro
    2420            2425            2430

Glu Gly Thr Thr Gly Gln Ser Tyr Asn Gln Tyr Ser Gln Arg Tyr
    2435            2440            2445

His Gln Arg Thr Asn Thr Asn Val Asn Cys Pro Ile Glu Cys Phe
    2450            2455            2460

Met Pro Leu Asp Val Gln Ala Asp Arg Glu Asp Ser Arg Glu
    2465            2470            2475

<210> SEQ ID NO 2
<211> LENGTH: 2478
<212> TYPE: PRT
<213> ORGANISM: Sus scrofa

<400> SEQUENCE: 2

Met Leu Gly Gly Pro Gly Pro Gly Leu Leu Leu Ala Val Leu Ser
1               5                   10                  15

Leu Gly Thr Thr Val Pro Ser Thr Gly Ala Ser Lys Ser Lys Arg Gln
            20                  25                  30

Ala Gln Gln Ile Val Gln Pro Gln Ser Pro Leu Val Asp Ser Gln Arg
        35                  40                  45

Lys Pro Gly Cys Tyr Asp Asn Gly Lys His Tyr Gln Ile Asn Gln Gln
    50                  55                  60

Trp Glu Arg Thr Tyr Leu Gly Ser Ala Leu Val Cys Thr Cys Tyr Gly
65                  70                  75                  80

Gly Ser Arg Gly Phe Asn Cys Glu Ser Lys Pro Glu Pro Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Gly Thr Ser Tyr Val Val Gly Glu Thr Trp Glu Lys Pro Tyr Gln Gly
        195                 200                 205

Trp Met Met Val Asp Cys Thr Cys Leu Gly Glu Gly Ser Gly Arg Ile
    210                 215                 220

Thr Cys Thr Ser Arg Asn Arg Cys Asn Asp Gln Asp Thr Arg Thr Ser
225                 230                 235                 240

Tyr Arg Ile Gly Asp Thr Trp Ser Lys Lys Asp Asn Arg Gly Asn Leu
                245                 250                 255

Leu Gln Cys Ile Cys Thr Gly Asn Gly Arg Gly Glu Trp Lys Cys Glu
            260                 265                 270

Arg His Thr Ser Leu Gln Thr Thr Ser Ala Gly Ser Gly Ser Phe Thr
        275                 280                 285

Asp Val Arg Thr Ala Ile Tyr Gln Pro Gln Pro His Pro Gln Pro Ala
    290                 295                 300

-continued

```
Pro Tyr Gly His Cys Val Thr Asp Ser Gly Val Tyr Ser Val Gly
305                 310                 315                 320

Met Gln Trp Leu Lys Thr Gln Gly Asn Lys Gln Met Leu Cys Thr Cys
                325                 330                 335

Leu Gly Asn Gly Val Ser Cys Gln Glu Thr Ala Val Thr Gln Thr Tyr
            340                 345                 350

Gly Gly Asn Ser Asn Gly Glu Pro Cys Val Leu Pro Phe Thr Tyr Asn
        355                 360                 365

Gly Arg Thr Phe Tyr Ser Cys Thr Thr Glu Gly Arg Gln Asp Gly His
    370                 375                 380

Leu Trp Cys Ser Thr Thr Ser Asn Tyr Glu Gln Asp Gln Lys Tyr Ser
385                 390                 395                 400

Phe Cys Thr Asp His Thr Val Leu Val Gln Thr Arg Gly Gly Asn Ser
                405                 410                 415

Asn Gly Ala Leu Cys His Phe Pro Phe Leu Tyr Asn Asn Arg Asn Tyr
            420                 425                 430

Thr Asp Cys Thr Ser Glu Gly Arg Arg Asp Asn Met Lys Trp Cys Gly
        435                 440                 445

Thr Thr Gln Asn Tyr Asp Ala Asp Gln Lys Phe Gly Phe Cys Pro Met
    450                 455                 460

Ala Ala His Glu Glu Ile Cys Thr Thr Asn Glu Gly Val Met Tyr Arg
465                 470                 475                 480

Ile Gly Asp Gln Trp Asp Lys Gln His Asp Met Gly His Met Met Arg
                485                 490                 495

Cys Thr Cys Val Gly Asn Gly Arg Gly Glu Trp Thr Cys Val Ala Tyr
            500                 505                 510

Ser Gln Leu Arg Asp Gln Cys Ile Val Asp Asp Ile Thr Tyr Asn Val
        515                 520                 525

Asn Asp Thr Phe His Lys Arg His Glu Glu Gly His Met Leu Asn Cys
    530                 535                 540

Thr Cys Phe Gly Gln Gly Arg Gly Arg Trp Lys Cys Asp Pro Val Asp
545                 550                 555                 560

Gln Cys Gln Asp Ser Glu Thr Arg Thr Phe Tyr Gln Ile Gly Asp Ser
                565                 570                 575

Trp Glu Lys Tyr Val His Gly Val Arg Tyr Gln Cys Tyr Cys Tyr Gly
            580                 585                 590

Arg Gly Ile Gly Glu Trp His Cys Gln Pro Leu Gln Thr Tyr Pro Gly
        595                 600                 605

Thr Thr Gly Pro Val Gln Val Ile Ile Thr Glu Thr Pro Ser Gln Pro
    610                 615                 620

Asn Ser His Pro Ile Gln Trp Asn Ala Pro Glu Pro Ser His Ile Ser
625                 630                 635                 640

Lys Tyr Ile Leu Arg Trp Lys Pro Lys Asn Ser Pro Asn Arg Trp Lys
                645                 650                 655

Glu Ala Thr Ile Pro Gly His Leu Asn Ser Tyr Thr Ile Lys Gly Leu
            660                 665                 670

Arg Pro Gly Val Val Tyr Glu Gly Gln Leu Ile Ser Val Gln His Tyr
        675                 680                 685

Gly His Arg Glu Val Thr Arg Phe Asp Phe Thr Thr Ser Thr Ser
    690                 695                 700

Ser Ala Val Thr Ser Asn Thr Val Val Gly Glu Thr Thr Pro Phe Ser
705                 710                 715                 720
```

```
Pro Val Val Ala Thr Ser Glu Ser Val Thr Glu Ile Thr Ala Ser Ser
            725                 730                 735

Phe Val Val Ser Trp Val Ser Ala Ser Asp Thr Val Ser Gly Phe Arg
            740                 745                 750

Val Glu Tyr Glu Leu Ser Glu Glu Gly Asp Glu Pro Gln Tyr Leu Asp
            755                 760                 765

Leu Pro Ser Thr Ala Thr Ser Val Asn Ile Pro Asp Leu Leu Pro Gly
            770                 775                 780

Arg Lys Tyr Ile Val Asn Val Tyr Gln Ile Ser Glu Glu Gly Glu Gln
785                 790                 795                 800

Ser Leu Ile Leu Ser Thr Ser Gln Thr Thr Ala Pro Asp Ala Pro Pro
            805                 810                 815

Asp Pro Thr Val Asp Gln Val Asp Thr Ser Ile Val Val Arg Trp
            820                 825                 830

Ser Arg Pro Gln Ala Pro Ile Thr Gly Tyr Arg Ile Val Tyr Ser Pro
            835                 840                 845

Ser Val Glu Gly Ser Ser Thr Glu Leu Asn Leu Pro Gly Thr Ala Asn
            850                 855                 860

Ser Val Thr Leu Ser Asp Leu Gln Pro Gly Val Gln Tyr Asn Ile Thr
865                 870                 875                 880

Ile Tyr Ala Val Glu Glu Asn Gln Glu Ser Thr Pro Val Phe Ile Gln
            885                 890                 895

Gln Glu Thr Thr Gly Val Pro Arg Pro Asp Lys Val Pro Pro Lys
            900                 905                 910

Asp Leu Gln Phe Val Glu Val Thr Asp Val Lys Val Thr Ile Met Trp
            915                 920                 925

Thr Pro Pro Glu Ser Pro Val Thr Gly Tyr Arg Val Asp Val Ile Pro
            930                 935                 940

Val Asn Leu Pro Gly Glu His Gly Gln Arg Leu Pro Ile Ser Arg Asn
945                 950                 955                 960

Thr Phe Ala Glu Val Thr Gly Leu Ser Pro Gly Val Thr Tyr His Phe
            965                 970                 975

Lys Val Phe Ala Val Asn Gln Gly Arg Glu Ser Lys Pro Leu Thr Ala
            980                 985                 990

Gln Gln Thr Thr Lys Leu Asp Ala Pro Thr Asn Leu Gln Phe Ile Asn
            995                 1000                1005

Glu Thr Asp Ser Thr Val Met Val Thr Trp Thr Pro Pro Arg Ala
            1010                1015                1020

Arg Ile Ala Gly Tyr Arg Leu Thr Val Gly Leu Thr Arg Gly Gly
            1025                1030                1035

Gln Pro Lys Gln Tyr Asn Val Gly Pro Ser Ala Ser Gln Tyr Leu
            1040                1045                1050

Leu Arg Asn Leu Gln Pro Gly Ser Glu Tyr Ala Val Thr Leu Val
            1055                1060                1065

Ala Val Lys Gly Asn Gln Gln Ser Pro Arg Ala Thr Gly Val Phe
            1070                1075                1080

Thr Thr Leu Gln Pro Val Gly Ser Ile Pro Pro Tyr Asn Thr Glu
            1085                1090                1095

Val Thr Glu Thr Thr Ile Val Ile Thr Trp Thr Pro Ala Pro Arg
            1100                1105                1110

Ile Gly Phe Lys Leu Gly Val Arg Pro Ser Gln Gly Gly Glu Ala
            1115                1120                1125
```

```
Pro Arg Glu Val Thr Ser Asp Ser Gly Ser Ile Val Val Ser Gly
1130                1135                1140

Leu Thr Pro Gly Val Glu Tyr Val Tyr Thr Ile Ser Val Leu Arg
1145                1150                1155

Asp Gly Gln Glu Arg Asp Thr Pro Ile Val Lys Lys Val Val Thr
1160                1165                1170

Pro Leu Ser Pro Pro Thr Asn Leu His Leu Glu Ala Asn Pro Asp
1175                1180                1185

Thr Gly Val Leu Thr Val Ser Trp Glu Arg Ser Thr Thr Pro Asp
1190                1195                1200

Ile Thr Gly Tyr Arg Ile Thr Thr Pro Thr Asn Gly Gln Gln
1205                1210                1215

Gly Tyr Ser Leu Glu Glu Val Val His Ala Asp Gln Ser Ser Cys
1220                1225                1230

Thr Phe Glu Asn Leu Ser Pro Gly Leu Glu Tyr Asn Val Ser Val
1235                1240                1245

Tyr Thr Val Lys Asn Asp Lys Glu Ser Val Pro Ile Ser Asp Thr
1250                1255                1260

Ile Ile Pro Glu Val Pro Gln Leu Thr Asp Leu Ser Phe Val Asp
1265                1270                1275

Ile Thr Asp Ser Ser Ile Gly Leu Arg Trp Thr Pro Ile Asn Ser
1280                1285                1290

Ser Thr Ile Ile Gly Tyr Arg Ile Thr Val Val Ala Ala Gly Glu
1295                1300                1305

Gly Ile Pro Ile Phe Glu Asp Phe Ala Asp Ser Ser Val Gly Tyr
1310                1315                1320

Tyr Thr Val Thr Gly Leu Glu Pro Gly Ile Asp Tyr Asp Ile Ser
1325                1330                1335

Val Ile Thr Leu Ile Asn Gly Gly Glu Ser Ala Pro Thr Thr Leu
1340                1345                1350

Thr Gln Gln Thr Ala Val Pro Pro Thr Asp Leu Arg Phe Thr
1355                1360                1365

Asn Val Gly Pro Asp Thr Ile Arg Val Thr Trp Ala Pro Pro Pro
1370                1375                1380

Ser Ile Glu Leu Thr Asn Phe Leu Val Arg Tyr Ser Pro Val Lys
1385                1390                1395

Asn Glu Glu Asp Val Ala Glu Leu Ser Ile Ser Pro Ser Asp Asn
1400                1405                1410

Ala Val Val Leu Thr Asn Leu Leu Pro Gly Thr Glu Tyr Leu Val
1415                1420                1425

Ser Val Ser Ser Val Tyr Glu Gln His Glu Ser Ile Pro Leu Arg
1430                1435                1440

Gly Arg Gln Lys Thr Gly Leu Asp Ser Pro Thr Gly Ile Asp Phe
1445                1450                1455

Ser Asp Ile Thr Ala Asn Ser Phe Thr Val Tyr Trp Ile Ala Pro
1460                1465                1470

Arg Ala Thr Ile Thr Gly Tyr Lys Ile Arg His His Pro Glu His
1475                1480                1485

Met Gly Gly Arg Pro Arg Glu Asp Arg Val Pro Pro Ser Arg Asn
1490                1495                1500

Ser Ile Thr Leu Thr Asn Leu Ile Pro Gly Val Glu Tyr Val Val
1505                1510                1515
```

-continued

Ser Ile Val Ala Val Asn Gly Arg Glu Glu Ser Pro Pro Leu Val
1520                1525                1530

Gly Gln Gln Ser Thr Val Ser Asp Val Pro Arg Asp Leu Gln Val
1535                1540                1545

Ile Ala Thr Thr Pro Thr Ser Leu Leu Ile Ser Trp Asp Ala Pro
1550                1555                1560

Ala Val Thr Val Arg Tyr Tyr Arg Ile Thr Tyr Gly Glu Thr Gly
1565                1570                1575

Gly Asn Ser Pro Val Gln Glu Phe Thr Val Pro Gly Ser Lys Ser
1580                1585                1590

Thr Ala Thr Ile Ser Gly Leu Lys Pro Gly Val Asp Tyr Thr Ile
1595                1600                1605

Thr Val Tyr Ala Val Thr Gly Arg Gly Asp Ser Pro Ala Ser Ser
1610                1615                1620

Lys Pro Val Ser Ile Asp Tyr Arg Thr Glu Ile Asp Lys Pro Ser
1625                1630                1635

Gln Met Gln Val Thr Asp Val Gln Asp Asn Ser Ile Ser Val Arg
1640                1645                1650

Trp Leu Pro Ser Ser Ser His Val Thr Gly Tyr Arg Val Thr Thr
1655                1660                1665

Thr Pro Lys Asn Gly Ser Gly Pro Ser Lys Thr Lys Thr Val Gly
1670                1675                1680

Pro Asp Gln Thr Glu Met Thr Ile Glu Gly Leu Gln Pro Thr Val
1685                1690                1695

Glu Tyr Val Val Ser Val Tyr Ala Gln Asn Gln Asn Gly Glu Ser
1700                1705                1710

Gln Pro Leu Val Gln Thr Ala Val Thr Asn Ile Asp Arg Pro Lys
1715                1720                1725

Gly Leu Ala Phe Thr Asp Val Asp Val Asp Ser Ile Lys Ile Ala
1730                1735                1740

Trp Glu Ser Pro Gln Gly Gln Val Ser Arg Tyr Arg Val Thr Tyr
1745                1750                1755

Ser Ser Pro Glu Asp Gly Ile His Glu Leu Phe Pro Ala Pro Asp
1760                1765                1770

Gly Glu Glu Asp Thr Ala Glu Leu Gln Gly Leu Arg Pro Gly Ser
1775                1780                1785

Glu Tyr Thr Val Ser Val Val Ala Leu His Asp Asp Met Glu Ser
1790                1795                1800

Gln Pro Leu Ile Gly Thr Gln Ser Thr Ala Ile Pro Ala Pro Thr
1805                1810                1815

Asn Leu Lys Phe Thr Gln Val Thr Pro Thr Ser Leu Thr Ala Gln
1820                1825                1830

Trp Thr Ala Pro Asn Val Gln Leu Thr Gly Tyr Arg Val Arg Val
1835                1840                1845

Thr Pro Lys Glu Lys Thr Gly Pro Met Lys Glu Ile Asn Leu Ala
1850                1855                1860

Pro Asp Ser Ser Ser Val Val Val Ser Gly Leu Met Val Ala Thr
1865                1870                1875

Lys Tyr Glu Val Ser Ile Tyr Ala Leu Lys Asp Thr Leu Thr Ser
1880                1885                1890

Arg Pro Ala Gln Gly Val Val Thr Thr Leu Glu Asn Val Ser Pro
1895                1900                1905

```
Pro Arg Arg Ala Arg Val Thr Asp Ala Thr Glu Thr Thr Ile Thr
1910                1915                1920

Ile Ser Trp Arg Thr Lys Thr Glu Thr Ile Thr Gly Phe Gln Val
1925                1930                1935

Asp Ala Val Pro Ala Asn Gly Gln Thr Pro Ile Gln Arg Thr Ile
1940                1945                1950

Lys Pro Asp Val Arg Ser Tyr Thr Ile Thr Gly Leu Gln Pro Gly
1955                1960                1965

Thr Asp Tyr Lys Ile Tyr Tyr Thr Leu Asn Asp Asn Ala Arg
1970                1975                1980

Ser Ser Pro Val Val Ile Asp Ala Ser Thr Ala Ile Asp Ala Pro
1985                1990                1995

Ser Asn Leu Arg Phe Leu Ala Thr Thr Pro Asn Ser Leu Leu Val
2000                2005                2010

Ser Trp Gln Pro Pro Arg Ala Lys Ile Thr Gly Tyr Ile Ile Lys
2015                2020                2025

Tyr Glu Lys Pro Gly Ser Pro Pro Arg Glu Val Val Pro Arg Pro
2030                2035                2040

Arg Pro Gly Val Thr Glu Ala Thr Ile Thr Gly Leu Glu Pro Ala
2045                2050                2055

Thr Glu Tyr Thr Ile Gln Val Ile Ala Leu Lys Asn Asn Gln Lys
2060                2065                2070

Ser Glu Pro Leu Ile Gly Arg Lys Arg Thr Asp Glu Leu Pro Gln
2075                2080                2085

Leu Val Thr Leu Pro His Pro Asn Leu His Gly Pro Glu Ile Leu
2090                2095                2100

Asp Val Pro Ser Thr Val Gln Lys Thr Pro Phe Val Thr Lys Pro
2105                2110                2115

Gly Tyr Asp Thr Gly Asn Gly Ile Gln Leu Pro Gly Thr Ser Gly
2120                2125                2130

Gln Gln Pro Ser Leu Gly Gln Gln Met Ile Phe Glu Glu His Gly
2135                2140                2145

Phe Arg Arg Thr Thr Pro Pro Thr Thr Ala Thr Pro Val Arg His
2150                2155                2160

Arg Pro Gly Pro Tyr Thr Pro Asn Val Asn Glu Glu Ile Gln Val
2165                2170                2175

Gly His Val Pro Arg Gly Asp Val Asp His His Leu Tyr Pro His
2180                2185                2190

Val Leu Gly Leu Asn Pro Asn Ala Ser Thr Gly Gln Glu Ala Leu
2195                2200                2205

Ser Gln Thr Thr Ile Ser Trp Thr Pro Phe Gln Glu Ser Ser Glu
2210                2215                2220

Tyr Ile Ile Ser Cys His Pro Val Gly Ile Asp Glu Glu Pro Leu
2225                2230                2235

Gln Phe Arg Val Pro Gly Thr Ser Ala Ser Ala Thr Leu Thr Gly
2240                2245                2250

Leu Thr Arg Gly Ala Thr Tyr Asn Ile Ile Val Glu Ala Leu Lys
2255                2260                2265

Asp Gln Lys Arg His Lys Ile Arg Glu Glu Val Val Thr Val Gly
2270                2275                2280

Asn Ser Val Asp Gln Gly Leu Ser Gln Pro Thr Asp Asp Ser Cys
2285                2290                2295
```

-continued

```
Phe  Asp  Pro  Tyr  Thr  Val  Ser  His  Tyr  Ala  Ile  Gly  Glu  Glu  Trp
2300                          2305                     2310

Glu  Arg  Leu  Ser  Glu  Ser  Gly  Phe  Lys  Leu  Ser  Cys  Gln  Cys  Leu
2315                          2320                     2325

Gly  Phe  Gly  Ser  Gly  His  Phe  Arg  Cys  Asp  Ser  Ser  Lys  Trp  Cys
2330                          2335                     2340

His  Asp  Asn  Gly  Val  Asn  Tyr  Lys  Ile  Gly  Glu  Lys  Trp  Asp  Arg
2345                          2350                     2355

Gln  Gly  Glu  Asn  Gly  Gln  Met  Met  Ser  Cys  Thr  Cys  Leu  Gly  Asn
2360                          2365                     2370

Gly  Lys  Gly  Glu  Phe  Lys  Cys  Asp  Pro  His  Glu  Ala  Thr  Cys  Tyr
2375                          2380                     2385

Asp  Asp  Gly  Lys  Thr  Tyr  His  Val  Gly  Glu  Gln  Trp  Gln  Lys  Glu
2390                          2395                     2400

Tyr  Leu  Gly  Ala  Ile  Cys  Ser  Cys  Thr  Cys  Phe  Gly  Gly  Gln  Arg
2405                          2410                     2415

Gly  Trp  Arg  Cys  Asp  Asn  Cys  Arg  Arg  Pro  Gly  Ala  Glu  Leu  Gly
2420                          2425                     2430

Pro  Glu  Gly  Ser  Thr  Gly  His  Ser  Tyr  Asn  Gln  Tyr  Ser  Gln  Arg
2435                          2440                     2445

Tyr  His  Gln  Arg  Thr  Asn  Thr  Asn  Val  Asn  Cys  Pro  Ile  Glu  Cys
2450                          2455                     2460

Phe  Met  Pro  Leu  Asp  Val  Gln  Ala  Asp  Ile  Glu  Asp  Ser  Arg  Glu
2465                          2470                     2475
```